United States Patent
Smith et al.

(10) Patent No.: US 10,344,052 B2
(45) Date of Patent: Jul. 9, 2019

(54) TARGETING PEPTIDES AND USES THEREOF

(71) Applicant: Health Research, Inc., Buffalo, NY (US)

(72) Inventors: Gary Smith, Buffalo, NY (US); Ryan Willard, Grand Island, NY (US)

(73) Assignee: Health Research, Inc., Buffalo, NY (US)

(*) Notice: Subject to any disclaimer, the term of this patent is extended or adjusted under 35 U.S.C. 154(b) by 231 days.

(21) Appl. No.: 14/774,834

(22) PCT Filed: Mar. 14, 2014

(86) PCT No.: PCT/US2014/027908
§ 371 (c)(1),
(2) Date: Sep. 11, 2015

(87) PCT Pub. No.: WO2014/152831
PCT Pub. Date: Sep. 25, 2014

(65) Prior Publication Data
US 2016/0046668 A1    Feb. 18, 2016

Related U.S. Application Data

(60) Provisional application No. 61/783,779, filed on Mar. 14, 2013.

(51) Int. Cl.
*A61K 38/00*    (2006.01)
*C07K 7/06*    (2006.01)
*C07K 7/08*    (2006.01)
*C12N 9/10*    (2006.01)

(52) U.S. Cl.
CPC .......... *C07K 7/06* (2013.01); *C07K 7/08* (2013.01); *C12N 9/1077* (2013.01); *A61K 38/00* (2013.01); *C07K 2319/40* (2013.01); *C07K 2319/55* (2013.01); *C12Y 204/02036* (2013.01)

(58) Field of Classification Search
CPC ........ C07K 7/06; C07K 7/08; C07K 2319/40; C07K 2319/55; C12N 9/1077; A61K 38/00
See application file for complete search history.

(56) References Cited

U.S. PATENT DOCUMENTS

| 2003/0092077 A1* | 5/2003 | Ramarao ............ C07K 14/4705 435/7.21 |
| 2008/0119444 A1 | 5/2008 | Lehrer |
| 2012/0045390 A1 | 2/2012 | Desauvage et al. |
| 2012/0207820 A1 | 8/2012 | Belogurov et al. |

FOREIGN PATENT DOCUMENTS

WO    WO2000/77031    * 12/2000    ............... C07K 7/00

OTHER PUBLICATIONS

Papadopoulos et al., Tumor Angiogenesis is Associated with MUC1 Overexpression and Loss of Prostate-specific Antigen Expression in Prostate Cancer, Clinical Cancer Research, vol. 7, 1533-1538, Jun. 2001.*
Frankel et al., Minireview, Targeted Toxins, Clin. Cancer Res. vol. 6, 326-334, Feb. 2000.*
Katoch et al., Structure of a Peptide Adsorbed on Graphene and Graphite, Nano Letters 2012, vol. 12(5), p. 2342-2346. Jan. 1, 2012.
Zhang et al., Interactions of graphene and graphene oxide with proteins and peptides, Nanotechnol. Rev. Feb. 2013, vol. 2(1), p. 24-45. Feb. 1, 2013.
Lu et al., General approach for monitoring peptide-protein interactions based on graphene-peptide complex, Anal. Chem. 2011, vol. 83(19), pp. 7276-7282. Jan. 1, 2011.
Yang et al., Graphene in mice: ultrahigh in vivo tumor uptake and efficient photothermal therapy, Nano Lett. 2010, vol. 10(9), p. 3318-23. Jan. 1, 2010.
Sanchez et al., Biological Interactions of Graphene-Family Nanomaterials—An Interdisciplinary Review, Chem. Res. Toxicol., 2012, vol. 25(1), p. 15-34. Jan. 1, 2012.
Ara et al., Development of a Novel DNA Aptamer Ligand Targeting to Primary Cultured Tumor Endothelial cells by a Cell-Based SELEX Method, PLoS One., 2012, vol. 7(12):e50174. Jan. 1, 2012.
Wei et al., Catalytic Peptides for Inorganic Nanocrystal Synthesis Discovered by New Combinatorial Phage Display Approach, Angew Chem Int Ed Engl., 2011, vol. 59(45), p. 10585-10588. Jan. 1, 2011.

* cited by examiner

*Primary Examiner* — Sudhakar Katakam
(74) *Attorney, Agent, or Firm* — Hodgson Russ LLP

(57) ABSTRACT

Provided are peptides, fusion proteins which include the peptide sequences, compositions comprising such peptides and fusion proteins, and methods for making and using the compositions. The peptides are characterized as being able to selectively bind to components of the endothelial compartment that are exposed during the period between 1 and 7 days after androgen deprivation.

5 Claims, No Drawings
Specification includes a Sequence Listing.

US 10,344,052 B2

TARGETING PEPTIDES AND USES THEREOF

CROSS REFERENCE TO RELATED APPLICATIONS

This application claims priority to U.S. application No. 61/783,779, filed Mar. 14, 2013, the disclosure of which is incorporated herein by reference.

STATEMENT REGARDING FEDERALLY SPONSORED RESEARCH

This invention was made with government support under CA077739 and HHSN261201000119C awarded by the National Institutes of Health, and W81XWH-04-1-0264 awarded by the United States Army Medical Research and Materiel Command. The government has certain rights in the invention.

FIELD OF THE INVENTION

The present invention relates generally to targeted peptide delivery and more specifically to novel peptides and conjugates thereof for use as therapeutic and imaging agents.

BACKGROUND OF THE INVENTION

There is an ongoing and unmet need to develop compositions and methods for targeting tissue architecture that is involved in disease etiology, and especially for vascular structures that are involved in the progression and/or treatment of cancer. The present invention meets these needs.

SUMMARY OF THE INVENTION

The present disclosure provides compositions and method related to novel peptides, method of making the peptides, fusion proteins comprising the peptides, peptides conjugated to detectable labels, and chemotherapeutic agents. In embodiments, the chemotherapeutic agents comprise or consist of polypeptide sequences.

The disclosure includes peptides and recombinant fusion proteins comprising them, wherein the peptide sequences include every peptide sequence disclosed herein. In embodiments, the disclosure includes a peptide having a peptide sequence selected from GAMHLPWHMGTL (SEQ ID NO:5), KPPQNTSAPYLP (SEQ ID NO:6); SPHWQPNAIFVN (SEQ ID NO:8); TLQRTHFPPAFS (SEQ ID NO:9), TMGFTAPRFPHY (SEQ ID NO:10), SPHWQPNAI (SEQ ID NO:19), and GAMHLPWHMGT (SEQ ID NO:100). In embodiments the peptide sequence does not comprise bacteriophage coat protein amino acid sequence. In embodiments, the peptide sequence is present in a fusion protein, wherein the fusion protein does not comprise bacteriophage coat protein. In embodiments, the fusion protein that comprises the peptide sequence comprises a detectable label, such as a radiolabel, or the fusion protein comprises a chemotherapeutic agent, including but not limited to chemotherapeutic agents that are enzymatically active toxins. It will be recognized by those skilled in the art that the peptides provided by the invention are artificial and have properties that make the markedly different from that which occurs in nature.

In one embodiment, the disclosure includes a peptide or fusion protein comprising the sequence of a peptide, wherein the peptide or fusion protein is bound to a human cell or tissue. Thus, complexes comprising the peptides/fusion proteins and human epithelial cells and tissues are included. In embodiments the complex is formed between a peptide or fusion protein comprising the peptide sequence and an endothelial cell and/or a component, such as a marker, of the vascular basement membrane. In embodiments, the peptide binding location is exposed during a period subsequent to initiation of androgen deprivation in a subject. Method of forming such complexes are included, and can be part of a prophylactic and/or therapeutic approach for prostate cancer and other prostate related disorders, such as benign prostatic hypertrophy (BPH). The disclosure is not necessarily limited to prostate disorders.

The disclosure also includes pharmaceutical compositions comprising a peptide having a peptide sequence disclosed herein. In embodiments, the peptides are conjugated to other agents. The pharmaceutical compositions comprise a pharmaceutically acceptable additive, including but not necessarily limited to a pharmaceutically acceptable carrier.

In one approach, the disclosure includes a method for prophylaxis and/or therapy of an individual in need thereof comprising administering to the individual a peptide having a peptide sequence disclosed herein, or fusion proteins comprising such peptide sequences, and compositions comprising such peptide sequences. In embodiments the individual is in need of therapy for prostate cancer or benign prostatic hypertrophy. In embodiments, the individual is undergoing androgen deprivation therapy.

The disclosure also includes all methods of making the peptides and fusion proteins and peptide conjugates, including by chemical synthesis and recombinant methods.

DETAILED DESCRIPTION OF THE INVENTION

The present disclosure provides compositions and methods that are useful for, among other purposes, specifically binding to certain markers that are exposed during a transient period the follows androgen deprivation therapy. In this regard, the disclosure provides peptides and methods of using the peptides for targeting tissue structures, and particularly for targeting epithelial cells, and endothelial cells, and the vascular basement membrane, particularly in prostate tissue. The invention accordingly provides compositions comprising the peptides and methods for using them in therapeutic interventions for treating diseases that include but are not necessarily limited to cancer, such as benign prostatic hypertrophy (hyperplasia).

The instant invention is based in part on our discovery of novel peptides that can target microvasculature in human prostate tissue exposed by androgen deprivation. In more detail, and as disclosed in U.S. Pat. No. 8,048,640, (the '640 patent) the disclosure of which is incorporated herein by reference, the vasculature of the human prostate is unique among organs that are major sites of human disease in that the endothelial compartment appears significantly less stable than the vascular compartment of other organs. The epithelial compartment of the prostate demonstrates a proliferative index as much as two orders of magnitude greater than other organs and as much as 50-70% of the small vessels in benign and malignant prostate lack association with vascular smooth muscle cells that signify vascular maturation and stability. Studies using human prostate xenografts transplanted to immunocompromised mouse as described in the '640 patent demonstrate that the endothelial cells of the human vasculature express androgen receptor, have a peak of apoptotic death at two days after androgen deprivation therapy, and disruption of the endothelial cells causes the vessels to leak plasma components into the interstitial space. The death of the endothelial compartment is followed by apoptotic death of the glandular epithelial compartment at 6-7 days after androgen deprivation. However, in response to the hypoxia induced by the rapid vascular involution, proliferation of the endothelial compartment with revascularization of the prostate tissue begins between 4 and 7 days after androgen-deprivation. Thus, the period between 1 and 7 days, and optimally between 1 and 4 days after androgen deprivation, represents an important but transient therapeutic window during which areas of labilized vasculature permit improved access to prostate cancer/epithelial cells.

In the present disclosure we harnessed this model in novel approaches to develop new peptides that can target the prostatic microenvironment exposed by androgen deprivation. Specifically, the experimental model in which the prostate-specific targeting peptides were identified were primary xenografts of human prostate cancer tissue transplanted to immuno-compromised mouse hosts that were pre-castrated and implanted with silastic tubing packed with testosterone to maintain human levels of circulating testosterone, and to allow the selective induction of androgen deprivation therapy (ADT) by removal of the silastic tubing. An important enabling characteristic of this model is that the vasculature of the xenografts is of human origin, and that the vascular endothelial cells undergo rapid apoptotic death in response to short-term androgen deprivation, resulting in transient destruction of the endothelial cell permeability barrier and access of a systemically introduced peptide library to endothelial cells, damaged endothelial cells, denuded vascular basement membrane and the interstitial tissue space including prostate cancer cells, benign prostate epithelial cells in benign prostatic hypertrophy (hyperplasia) and prostate cancer stem cells/benign prostate stem cells. The loss of the vascular permeability barrier allows access of large molecules into the interstitial tissue space, such as fibrin, indicating that the peptides will have access to all cellular types within the prostate tissue space, such as endothelial cells and vascular basement membrane.

The peptides of the invention include but are not limited to peptides comprising or consisting of amino acid sequences disclosed herein, fragments of the amino acid sequences, and modifications of peptides. In certain embodiments, peptides encompassed within the scope of the invention will function as agents that can bind to certain target tissues and/or cells. In certain embodiments, peptides of the invention will function to bind to tissue which comprises a human prostatic microenvironment. In certain embodiments, a peptide of the invention will selectively or specifically bind to human prostatic microenvironment exposed by androgen deprivation. In embodiments, a peptide of the invention, including in embodiments a fusion protein comprising a peptide sequence of the invention, will form a complex with a human endothelial cell or vascular basement membrane. The vascular basement membrane is understood to those skilled in the art. In general, it is a thin sheet of fibers, i.e., a matrix, that underlies the epithelium, which lines the cavities and surfaces of organs, or the endothelium which lines the interior surface of blood vessels. It is expected that the peptides disclosed herein can be modified and still retain these desirable properties. In this regard, the invention includes peptides of various lengths, and with various amino acid substitutions. For example, the invention includes peptides which have been modified by conservative amino acid substitutions that are based generally on relative similarity of R-group substituents. Non-limiting examples of such substitutions contemplated in the present invention include, but are not limited to: gly or ser for ala; lys for arg; gln or his for asn; glu for asp; ser for cys; asn for gln; asp for glu; ala for gly; asn or gln for his; leu or val for ile; ile or val for leu; arg for lys; leu or tyr for met; thr for ser; tyr for trp; phe for tyr; and ile or leu for val. Thus, peptides that comprise any single conservative amino acid substitution, or any combination of conservative amino acid substitutions, are included in the invention. Any peptide provided by the invention can comprise one, two, three, four, or five conservative amino acid substitutions.

Non-conservative substitutions that enhance desirable characteristics of the peptides, such as their capability to bind to human epithelial cells and/or human prostatic microenvironment, activity, circulation time, bioavailability, stability, targeting, imaging properties, etc., are also included in the invention.

In addition to amino acid substitutions, peptides of the invention may include fragments of any of the peptides described herein. Any peptide encompassed within the scope of the invention can comprise or consist of from 4-20 amino acids, inclusive, and including all integers there between. In certain embodiments, the peptides are 12-mers.

To the extent that any of the peptides/fragment sequences per se have been previously described, the present disclosure includes their use in methods for tissue targeting, diagnostic imaging, therapeutic interventions, and as pharmaceutical preparations, and in fusion proteins, where the fusion protein is distinct from any protein wherein a sequence of a peptide disclosed herein was included.

Each peptide sequence disclosed in the Tables provided herein is included within the scope of the invention. Compositions comprising any one of such peptides, or any combinations or subcombinations of them, are included in the invention. Thus, the invention includes compositions which include all, or only include one or some of the peptides disclosed herein. In certain aspects, the invention includes at least one of the ten distinct peptide sequences having the consensus sequences, as depicted in Table 1. The peptides comprising the consensus sequences are: KPPQNTSAPYLP (SEQ ID NO:6); TLQRTHFPPAFS (SEQ ID NO:9), TMGFTAPRFPHY (SEQ ID NO:10), SPHWQPNAIFVN (SEQ ID NO:8); and SPHWQPNAI (SEQ ID NO:19), which is a fragment of SEQ ID NO:8. In addition to these peptide sequences, the sequence GAMHLPWHMGTL (SEQ ID NO:5) exhibited high recovery, as further described below and in Table 2. In one embodiment, the M in position 9 of SEQ ID NO:5 is replaced with I to give GAMHLPWHIGTL (SEQ ID NO:101. In one embodiment, the peptide of SEQ ID NO:5 does not include the C-terminal L (GAMHLPWHMGT—SEQ ID NO:100). Each of these consensus sequences permits certain diversity in sequence but still retains function as indicated by their having been selected in vivo as described in further detail above.

It is also contemplated that the peptides of the present invention may include additional amino acids, and may include modified amino acids that can improve any desirable property of the peptides. Thus, the peptide sequences presented herein could be part of larger polypeptides or proteins, such as fusion proteins, or they could be connected to other moieties. Accordingly, the peptides could be covalently or non-covalently associated with any desirable moiety that would be expected to improve their functional capabilities in accordance with the method of the invention. In this regard, the peptides of the invention are expected to have utility in at least tissue targeting and/or diagnostic imaging applications and can therefore be modified for these purposes. In the case of fusion proteins, a peptide having a peptide sequence selected from any of the peptide sequences disclosed herein can be present in the fusion protein. Thus it will be apparent that a peptide described herein can include a peptide sequence within the context of a fusion protein. In embodiments, the peptides and the fusion protein do not comprise any bacteriophage coat protein amino acid sequence. Bacteriophage proteins are well known in the art. In embodiments, the peptides and fusion proteins do not comprise any pIII bacteriophage. In embodiments, the peptides do not comprise any Ml, or fd filamentous phage, or T4 or T7, or λ, phage protein. In embodiments In embodiments, the peptides and fusion proteins do not comprise any phagemid protein or protein that is encoded by a phagemid, other than sequence of the peptide.

In one embodiment, the peptides can be coupled with a chemotherapeutic agent, or any other agent that has cytotoxic activity. For example, chemotherapeutic agents useful in the generation of such peptide conjugates include enzymatically active toxins and fragments thereof. Suitable enzymatically active toxins include docetaxel, mitoxanthrone, taxanes, diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes, or any anti-angiogenic agent(s). In embodiments, the chemotherapeutic agents comprise or consist of polypeptides having enzymatic activity. In embodiments, the peptide is present at the amino-terminal end of the fusion protein. In embodiments, the N-terminal amino acid of a peptide disclosed herein is the N-terminus of a fusion protein, although the peptide can be positioned elsewhere in the fusion protein if desired, such as at the C-terminus, or within the fusion protein.

Conjugates of the peptide and chemotherapeutic agents may be made using a variety of bifunctional protein coupling agents such as N-succinimidyl-3-(2-pyriyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as his (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene).

In another embodiment, the peptides can be conjugated to a radioactive agent. A variety of radioactive isotopes are available for conjugating to peptides such that cells or tissues to which the peptides bind can be imaged or selectively destroyed. For selective destruction of cells the peptides can be conjugated to a highly radioactive atom, such as $At^{211}$, $I^{131}$, $I^{125}$, $Y^{90}$, $Re^{186}$, $Re^{188}$, $sm^{153}$, $Bi^{212}$, $P^{32}$, $Pb^{212}$ and radioactive isotopes of Lu. For identifying cells, such as prostate cancer cells, or cells in metastatic foci or in tumors, the peptide conjugates can include a radioactive atom for scintigraphic studies, for example $Tc^{99m}$ (metastable technetium-99), $I^{123}$, or a spin label for nuclear magnetic resonance and/or magnetic resonance imaging, such as $I^{123}$, $I^{131}$, $In^{111}$, $F^{19}$, $C^{13}$, $N^{15}$, $O^{17}$ or Gadolinium (III) or Manganese (II). The radio-labels may be incorporated in the peptides in known ways.

The use of peptides for identification of targeted tissues/cells can be performed using any suitable technique, given the benefit of the present disclosure. In certain embodiments, labeled peptides can be injected into patients diagnosed with or suspected of having a disease, such as a cancer. Information from such imaging can be used for diagnosing or staging of the disease status of the patient. The label used can be selected in accordance with the imaging system to be used. For example, $Indium^{111}$, $Technetium^{99}$ or $Iodine^{131}$ can be used for planar scans or single photon emission computed tomography (SPECT). Positron emitting labels such as $Fluorine^{19}$ can be used in positron emission tomography. Paramagnetic ions such as Gadolinium (III) or Manganese (II) can used in magnetic resonance imaging (MRI). Localization of the label within a particular tissue of the individual permits identification of locations which the peptides have targeted.

Therapeutic formulations comprising conjugated or unconjugated peptides of the invention may be prepared by mixing with pharmaceutically acceptable carriers, excipients or stabilizers in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). In certain embodiments, compositions of the invention can include distinct peptides, and can include mixtures of peptides, and can include linear (non-cyclic) and cyclic peptides.

Compositions comprising the peptides can include other therapeutic agents, such as conventional chemotherapeutic agents. Further, any suitable pharmaceutical delivery vehicle can be used to enhance delivery and/or efficacy of the peptides.

The peptides may be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In certain embodiments, the peptides are administered to an individual diagnosed with or suspected of having prostate cancer to inhibit metastasis or to inhibit the growth of the prostate cancer, or to patients with benign prostatic hypertrophy (hyperplasia) to inhibit growth of a benign lesion.

The peptides of the invention can be prepared by any technique known to those skilled in the art or by techniques hereafter developed. For example, the peptides can be prepared using the solid-phase synthetic technique (Merrifield, J. Am. Chem. Soc., 15:2149-2154 (1963); M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985). The synthesis of peptides by solution methods may also be used, as described in The Proteins, Vol. II, 3d Ed., p. 105-237, Neurath, H., et al., Eds., Academic Press, New York, N.Y. (1976). The synthesized peptides may be substantially purified by preparative high performance liquid chromatography or other comparable techniques available in the art. The composition of the synthetic peptides can be confirmed by an technique for amino acid composition analysis. The peptides can also be made using any suitable recombination system. Thus, in embodiments, the disclosure includes expression vectors encoding the peptide sequences, cells comprising the expression vectors, and methods of making the peptides comprising separating the peptides and/or fusion proteins comprising the peptide sequences from a recombinant expression system. In embodiments, the expression system is not a bacteriophage expression system. Every polynucleotide encoding the peptide sequences of this disclosure are encompassed herein, and in particular embodiments such polynucleotide sequences are provided in expression vectors.

In one embodiment, the invention provides a method of inhibiting angiogenesis and/or tumor growth and/or metastasis. The method comprises administering a composition comprising one or more of the peptides of the invention, wherein the peptides may or may not comprise a cytotoxic agent, to an individual in an amount effective to inhibit to inhibit tumor growth and/or inhibit metastasis. In another embodiment, the invention provides a method for imaging a tissue and/or one or more cells. The method comprises administering a composition comprising one or more labeled peptides of the invention and detecting localized labeled peptide via any suitable imaging apparatus or method The following techniques for phage selection, identification and production of peptides were used.

Biological System:

Male SCID mice were castrated and pre-implanted with silastic tubing to provide sustained-release of testosterone to maintain human serum levels testosterone in the host mouse and to facilitate castration/androgen deprivation (ADT). Human prostate tumor tissue was prepared for transplantation by cutting the radical prostatectomy surgical remnant in ViaSpan into approximately 1.0 mm$^3$ to 2.0 mm$^3$ wedges. Tissue was transplanted, into individual incisions in the skin; four pieces of tissue were transplanted on each flank of mice anesthetized with isoflurane. Each piece of tumor tissue was dipped into Matrigel, inserted into an incision, and the incisions closed with tissue glue.

Anastamosis of the human vasculature of the prostate cancer xenografts to the host mouse vascular system occurred between Days 5 and 6 after tissue transplantation, and the vasculature had stabilized by Day 21 after transplantation. Initiation of ADT by removal of the silastic tubing containing testosterone at a time point between Day 30 and Day 45 after transplantation with tissue resulted in acute apoptotic death of human endothelial cells in the microvasculature of the prostate cancer xenografts. The ADT-induced involution of human prostate endothelial cells produced a "therapeutic window" during which vascular leakage of serum components into the interstitial tissue space was demonstrated using systemically administered fluorescent lectin, leakage of MRI contrast dye (Gd-DTPA or Magnavist), or deposition of fibrin/fibrinogen.

Seventy-two hours after initiation of ADT, the host mouse was anesthetized with acepromazine/ketamine/xylazine and the peptide-phage display library introduced systemically by intra-cardiac injection into the right ventricle. The Ph.D.-12 phage library (NEB, Ipswich, Mass.) was injected at a concentration of $1.2 \times 10^{11}$ pfu in 100 µL. The phage library was allowed to circulate through the mouse host for 15 minutes. At the conclusion of the incubation the vascular volume was replaced by perfusion (40 ml) with PBS to remove unbound phage. During perfusion viable xenografts that anastomosed to the host vasculature were observed to blanche. The xenografts were excised and placed into an eppendorf tube containing 0.5 mL phage elution buffer (0.2 M Glycine-HCl pH 2.2, 0.5% BSA) and the xenografts homogenized with a rotor/stator homogenizer on ice. The phage containing homogenate was cleared by centrifugation at 20,800×G for 5 minutes, and neutralization buffer (Tris-HCl pH 9.1) added to the supernatant. The concentration of phage in the eluate was established by titration: serial 10-fold dilutions of the neutralized phage eluate (10 µl) were added to 200 µL of a mid-log culture of host bacteria (ER2738), the cells/phage mixed with 3.5 mL of molten top agar (48° C.), and plated onto LB. Plates were incubated at 37° C. overnight and blue plaques were counted for determination of pfu. Based on the pfu, an aliquot of the neutralized phage eluate that contained a standardized number of phage was amplified by addition to a 20 mL flask of LB/Tet inoculated with 200 µL of an overnight culture of ER2738, and the culture incubated for 4 hours. The culture was cleared of bacteria by centrifugation, the supernatant treated with ⅙ volume of PEG/NaCl (20% (w/v) PEG-8000, 2.5M NaCl), refrigerated overnight for phage precipitation, and phage recovered by centrifugation. The final phage pellet was resuspended in 200 mL of TBS and titered (as described above). For all in vivo selections the input phage held constant at $1.2 \times 10^{11}$ phage per mouse.

Identification of Candidate Peptides:

Following the third sequential round of in vivo selection against tissue from a single patient, the recovered phage population was titered, diluted and plated at a concentration to yield approximately 100 plaques per plate. Individual plaques were picked and amplified for conventional DNA sequencing to verify that a diversity of peptides was selected. Subsequently, the region of the phage genome that contained the random peptides embedded in the pIII protein were amplified by PCR from all selected phage libraries in preparation for Next Gen Sequencing. PCR primers were designed that flanked the hyper-variable region of the phage genome, the region containing the peptide inserted into the pIII protein: (FWD:—3gIII: 5'-CCT TTC TAT TCT CAC TCT GCT-3' (SEQ ID NO:98); REV:—155gIII: 5'-CCG TAA CAC TGA GTT TCG TCA-3' (SEQ ID NO:99)). The amplified segments were the templates for the NextGen DNA sequencing process. Templates were quantified and concentrations normalized and underwent 454 Next Gen sequencing using 500 ng of amplified template DNA at a concentration of 50 ng/mL. Raw data from the NextGen sequencing were analyzed to identify the DNA base sequence of the hyper-variable region in both the forward and reverse compliment strands to assure that all selected peptides were identified. The DNA base sequence was translated, the amino termini of peptides aligned, and the final data set evaluated to quantitate the number of times each peptide was recovered in each library. The data sets for the individual patients were compared to identify peptides recovered in all, or the majority, of the individual prostate cancer tissue specimens.

Construction of Peptide Display Vectors (pMAL-pIII):

The NEB PhD phage phage display libraries were constructed by insertion of a random peptide library into a KpnI/EagI site directly adjacent to the 5' leader signal sequence of the pIII gene in the M13 phage. Therefore, the peptide is displayed as the amino-terminal end of the peptide-pIII fusion protein. NEB sells an expression vector (pMAL-PIII) that utilizes the same KpnI/EagI restriction sites the flank the peptide sequence in the phage to allow transfer of a peptide of interest from the phage genome into the expression vector. The peptide is expressed as the amino-terminus portion of a peptide/Maltose Binding Protein (MBP) fusion protein. The expression construct can produce milligrams of purified fusion protein from a 500 ml culture.

Oligonucleotide duplexes that contained candidate peptides of interest were designed to contain a 3' triple glycine spacer, KpnI/EagI restriction sites and additional random nucleotides capping each end of the sequence. The oligonucleotide duplexes were used to construct a peptide/Maltose Binding Protein fusion by insertion into the pMAL-PIII vector. The pMAL-PIII vector was linearized by digestion with Acc65I and EagI-HF in NEBuffer3/BSA for 60 minutes. The linearized vector is gel purified, the duplex oligonucleotides containing the candidate peptides were ligated into the pMAL-PIII vector, and the vector containing the fusion protein construct transformed into NEB Turbo Competent E. coli. Plasmid DNA was obtained from colonies with a Qiagen plasmid mini-prep kit and the presence of the correct insert confirmed by conventional DNA sequencing.

pMAL Fusion-Peptide Expression and Affinity Purification:

The fusion protein is expressed in the cytoplasm, where the pIII leader sequence aids in the translocation of the protein into the periplasmic space for post-translational removal of the leader sequence. Osmotic shock of the bacteria was used to release selective the processed fusion-protein from the periplasmic space. The cell lysate containing the fusion protein was applied to amylose-agarose beads (resin) that reversibly binds Maltose binding protein, and after washing the fusion protein was competitively eluted with 10 mM maltose.

The construct containing the peptide of interest was transformed into NEB Express cells, a protease-deficient bacterial strain. Transformed cells were propagated in f LB/AMP (100 µg/mL)+glucose (2.0 g/L to suppress the maltose genes on the bacterial chromosome, one of which will degrade the amylase affinity resin. At the conclusion of the culture the cell pellet was resuspended in ice-cold 5 mM $MgSO_4$, the slurry shaken in an ice bath, and the cell debris removed by centrifugation. The supernatant, the cold osmotic shock fluid that contains the fusion protein, was stabilized by addition of protease inhibitors and EDTA, and refrigerated until purification of the peptide-maltose binding protein fusion by affinity chromatography using amylose resin. After loading and washing, the fusion protein was competed off the amylose affinity matrix with a 10 mM maltose buffer. Fractions containing protein were concentrated to approximately 2.0 mg/ml, and glycerol added to a final concentration of 50% (1.0 mg/mL final protein concentration).

Identification of Candidate Peptides Specific for Binding to ADT-Damaged Prostate Microvascular Targets.

An aliquot of each the phage libraries recovered after one, two and three rounds of selection in vivo for binding to ADT-perturbed human prostate cancer vasculature underwent NextGen Sequence analysis. The average number of individual DNA sequences that contained peptide inserts reported for each of the 15 selected phage populations was 13,568. The DNA base sequences were converted to amino acid sequences, and the individual populations evaluated for the number of times each peptide was recovered to evaluate for enrichment across the three rounds of in vivo selection, and to identify peptides recovered in common across multiple patient specimens. All peptides selected as candidates for targeting ADT-perturbed prostate cancer microvasculature/tissue demonstrated progressive enrichment through the three sequential rounds of selection.

The peptides are expressed in the pIII coat protein of the phage (5 copies per phage) as a random 12 mer (12 amino acids). The 5'-end of the coding sequence for the random peptides starts at the conclusion of a leader sequence, which is clipped during expression on the phage coat. Therefore, the 5'-end of the peptide is free in solution. Consequently, the regions of conserved homology usually were located at the $NH_3$-terminus of the peptide, with various amounts of sequence diversity (degeneracy) present in the 3'-end of select peptides that share homology at the 5'-end.

TABLE 1

Candidate Targeting Peptides

| High-Priority Candidates |
|---|
| AETVESCLAKSH (SEQ ID NO: 1) |
| APGTLPWASSNR (SEQ ID NO: 2) |
| DAQSIYHFALAP (SEQ ID NO: 3) |
| DPKFPQNSHLIT (SEQ ID NO: 4) |
| GAMHLPWHMGTL (SEQ ID NO: 5) |
| KPPQNTSAPYLP (SEQ ID NO: 6) |
| SHAHNSTTFLLA (SEQ ID NO: 7) |
| SPHWQPNAIFVN (SEQ ID NO: 8) |
| TLQRTHFPPAFS (SEQ ID NO: 9) |
| TMGFTAPRFPHY (SEQ ID NO: 10) |

| Second Tier of Candidates |
|---|
| AELLKLFSKSHT (SEQ ID NO: 11) |
| VDAPLKSPLTAA (SEQ ID NO: 12) |
| AGNGTATATERT (SEQ ID NO: 13) |
| HGLPVTTRGAFG (SEQ ID NO: 14) |
| RLVNSSYLQLAS (SEQ ID NO: 15) |
| SFRTLTDWNVTL (SEQ ID NO: 16) |
| SPPPSHPSSGYL (SEQ ID NO: 17) |
| THHHVTYWRSEA (SEQ ID NO: 18) |

Ten consensus peptides were identified as "high priority" candidates, and eight peptides were selected as "second tier" candidates. The peptides are listed in Table 1. The use of the terms "high priority" and "second tier" are used herein to reflect rank of interest and proposed order of study and are not meant to diminish the importance of second tier peptides which are encompassed within the scope of this disclosure.

The parental library also was subjected to NextGen sequence analysis. The ten "high priority" candidate peptides were distributed randomly among the $10^9$ peptides present in the parental phage library: none of the selected peptides were enriched relative to all of the random peptides displayed in the library. However, the ten "high-priority" candidate peptides accounted for ~66% of the peptides recovered in the DNA sequence data sets after three rounds of selection in vivo for the two individual prostate cancer tissue specimens (Table 2), suggesting high levels of enrichment for these peptides as candidates capable of targeting specific epitopes unmasked or created by ADT.

For the high-priority candidates that were represented most frequently in the recovered peptides across all rounds of selection, not only was the consensus peptide recovered (the specific peptide recovered with the highest frequency), but multiple derivatives with small changes in the consensus sequence also were recovered. Table 3 presents a numerical tabulation of the recovery patterns from the individual in vivo selections after combining the data from the third round of selection for the two tumor specimens. The recovery of multiple degenerative derivatives of the consensus peptide provides evidence that the core sequence was selected specifically, and helps define the minimal core sequence necessary for maintenance of high-affinity binding to "epitopes" in the prostate cancer microvasculature and interstitial tissue.

TABLE 2

Recovery of Candidate Peptides

| Consensus Sequence | Percent of Total Phage After 3 Cycles of Selection | |
|---|---|---|
| | CaP Tissue Specimen 1 | CaP Tissue Specimen 2 |
| TLQRTHFPPAFS (SEQ ID NO: 9) | 9.58% | 7.57% |
| TMGFTAPRFPHY (SEQ ID NO: 10) | 26.5% | 4.78% |
| SPHWQPNAI (SEQ ID NO: 19) | 3.29% | 1.53% |
| AETVESCLAKSH (SEQ ID NO: 1) | 0.99% | 0.5% |
| KPPQTNTSAPYLP (SEQ ID NO: 20) | 27.3% | 5.48% |
| DQHGFMHIFDL (SEQ ID NO: 21) | 0.4% | 0.1% |
| GAMHLPWHMGT (SEQ ID NO: 100) | 0.21% | 46.3% |
| DPKFPQNSHLIT (SEQ ID NO: 4) | 0.63% | 0.35% |
| HSAQPVKSKAWL (SEQ ID NO: 22) | 0.3% | 0.2% |
| LLADTTHHRWT (SEQ ID NO: 23) | 0.1% | 0.1% |

TABLE 3

Diversity of Related Peptides Recovered Define the Consensus Ligand Sequence and Allowable Variation

| Peptide | # clones recovered |
|---|---|
| TLQRTHFPPAFS (SEQ ID NO: 9) | 7988 |
| TLQRTHFPPAFR (SEQ ID NO: 24) | 126 |
| TLQRTHFSAGVF (SEQ ID NO: 25) | 116 |
| TLQRTHFRRRFG (SEQ ID NO: 26) | 95 |
| TLQRTHFPSG (SEQ ID NO: 27) | 47 |
| TLQRTHFPSGVF (SEQ ID NO: 28) | 32 |
| TLQRTLFSAGRF (SEQ ID NO: 29) | 32 |
| TLQRTHFPPA (SEQ ID NO: 30) | 30 |
| TLQRTHFPPAFF (SEQ ID NO: 31) | 22 |
| TLQRTHFRPAFR (SEQ ID NO: 32) | 21 |
| TLQRTHFPPVVF (SEQ ID NO: 33) | 19 |
| TLQRTHFPSGV (SEQ ID NO: 34) | 19 |
| TLQRTHFPSGVS (SEQ ID NO: 35) | 14 |
| TLQRTLFPPVVS (SEQ ID NO: 36) | 14 |
| TLQRTLFSAGVF (SEQ ID NO: 37) | 9 |
| TLQRTHFPPVVS (SEQ ID NO: 38) | 8 |
| TLQRTHFPRRFR (SEQ ID NO: 39) | 6 |
| TLQRTHFPSA (SEQ ID NO: 40) | 6 |
| TLQRTHFRPAF (SEQ ID NO: 41) | 6 |
| TLQRTHFPPGVF (SEQ ID NO: 42) | 5 |
| TLQRTHFRRRF (SEQ ID NO: 43) | 5 |
| TLQRIHFPPAFS (SEQ ID NO: 44) | 5 |
| TLQRTHFSPAFS (SEQ ID NO: 45) | 4 |
| TLQRTHFSVR (SEQ ID NO: 46) | 4 |
| TLQRTHFPPAFW (SEQ ID NO: 47) | 3 |
| TLQRTHFPPAFP (SEQ ID NO: 48) | 3 |
| TLQRTHFPPAAG (SEQ ID NO: 49) | 3 |
| TLQRTHFPPARR (SEQ ID NO: 50) | 3 |
| TLQRTHFPLAFS (SEQ ID NO: 51) | 3 |
| TLQRTHFPRLFG (SEQ ID NO: 52) | 3 |

TABLE 3 -continued

Diversity of Related Peptides Recovered Define the Consensus Ligand Sequence and Allowable Variation

| Peptide | # clones recovered |
|---|---|
| TLQRTHFPRRFG (SEQ ID NO: 53) | 3 |
| SPHWQPNAIFVN (SEQ ID NO: 8) | 36 |
| SPHWQPNAILLM (SEQ ID NO: 54) | 17 |
| SPHWQPNAILL (SEQ ID NO: 55) | 2 |
| SPHWQPNAIL (SEQ ID NO: 56) | 2 |
| KPPQNTSAPYLP (SEQ ID NO: 6) | 659 |
| KPPQNTSAPLSS (SEQ ID NO: 57) | 3 |
| KPPQNTSAPYLR (SEQ ID NO: 58) | 2 |
| KPPQNTSAPY (SEQ ID NO: 59) | 2 |
| KPPQNTSCAFIF (SEQ ID NO: 60) | 2 |
| TMGFTAPRFPHY (SEQ ID NO: 10) | 641 |
| TMGFTAPRFPSL (SEQ ID NO: 61) | 9 |
| TMGFTAPRFSAL (SEQ ID NO: 62) | 3 |
| TMGLTHSRVRIE (SEQ ID NO: 63) | 2 |
| TMGFTAPRFPHY (SEQ ID NO: 10) | 3466 |
| TXGFTAPRFPHY (SEQ ID NO: 64) | 47 |
| TMGFTAPRFPSL (SEQ ID NO: 65) | 27 |
| TMGFTAPRFSAL (SEQ ID NO: 66) | 22 |
| TMGFTAPRFP (SEQ ID NO: 67) | 9 |
| TMGFTAPRFPHQ (SEQ ID NO: 68) | 8 |
| TMGFTAPRFPLL (SEQ ID NO: 69) | 6 |
| TMGFTAPRFRIM (SEQ ID NO: 70) | 5 |
| TMGFTAPRFPHL (SEQ ID NO: 71) | 4 |
| TMGFTAPRFPHR (SEQ ID NO: 72) | 4 |
| TMGFTAPRFPHH (SEQ ID NO: 73) | 3 |
| TMGFTAPRFPSV (SEQ ID NO: 74) | 2 |
| TMGFTAPRFPAL (SEQ ID NO: 75) | 2 |
| TMGFTAPRFPHC (SEQ ID NO: 76) | 2 |
| TMGFTAPRFPHM (SEQ ID NO: 77) | 2 |
| TMGFTAPRFQHY (SEQ ID NO: 78) | 2 |
| TMGFTAPRRGAV (SEQ ID NO: 79) | 2 |
| TMGFTAPWFPHY (SEQ ID NO: 80) | 2 |

Consensus Sequence = sequence in BOLD

The "second-tier" candidates were selected from a group of peptides that were selected in vivo from all the CaP specimens. However, for these peptides, related or degenerate peptides with a common/shared consensus region, but with areas of divergence, were not observed (Table 4). Furthermore, none of these peptides represented more 1.2% of the total peptides recovered after the third round of in vivo selection. The eight candidate peptides were selected arbitrarily from this group because they represented the most frequently observed of this group of candidates (highlighted by italics).

TABLE 4

Single Sequence Peptides Recovered in All Specimens

| | | | | | | | | | | | | |
|---|---|---|---|---|---|---|---|---|---|---|---|---|
| A | E | L | L | K | L | F | S | K | S | H | T | SEQ ID NO: 11 |
| A | P | G | T | L | P | W | A | S | S | N | R | SEQ ID NO: 2 |
| A | G | N | G | T | A | T | A | T | E | R | T | SEQ ID NO: 3 |
| A | H | T | T | N | S | S | N | Y | R | F | T | SEQ ID NO: 81 |
| D | A | Q | S | I | Y | H | F | A | L | A | P | SEQ ID NO: 3 |
| D | P | S | L | D | N | H | S | G | P | I | K | SEQ ID NO: 82 |
| E | A | A | I | T | L | P | M | T | S | W | T | SEQ ID NO: 83 |
| E | L | S | T | K | P | K | A | V | V | P | Y | SEQ ID NO: 84 |
| G | S | E | S | S | H | L | Y | E | K | P | K | SEQ ID NO: 85 |
| H | G | L | P | V | T | T | R | G | A | F | G | SEQ ID NO: 14 |
| I | P | A | P | A | S | M | L | K | P | P | R | SEQ ID NO: 86 |
| K | P | H | F | L | N | Q | S | G | S | Y | I | SEQ ID NO: 87 |
| L | P | Y | R | T | T | H | I | G | P | L | P | SEQ ID NO: 88 |
| L | Q | S | T | S | P | A | Y | T | H | R | M | SEQ ID NO: 89 |

TABLE 4-continued

Single Sequence Peptides Recovered in All Specimens

| | | | | | | | | | | | | |
|---|---|---|---|---|---|---|---|---|---|---|---|---|
| N | H | A | V | N | K | W | T | L | S | H | A | SEQ ID NO: 90 |
| Q | P | R | P | T | Q | Y | Q | E | H | S | A | SEQ ID NO: 91 |
| Q | L | T | G | P | T | G | M | K | T | P | L | SEQ ID NO: 92 |
| R | L | V | N | S | S | Y | L | Q | L | A | S | SEQ ID NO: 15 |
| S | P | P | P | S | H | P | S | S | G | Y | L | SEQ ID NO: 17 |
| S | F | R | T | L | T | D | W | N | V | T | L | SEQ ID NO: 16 |
| S | H | A | H | N | S | T | T | F | L/C | L/W | A/R | SEQ ID NO: 93 |
| S | T | A | G | P | M | F | P | Q | Q | S | R | SEQ ID NO: 94 |
| T | H | H | H | V | T | Y | W | R | S | E | A | SEQ ID NO: 18 |
| T | H | P | G | S | S | M | R | H | T | H | H | SEQ ID NO: 95 |
| T | H | S | H | G | L | K | P | S | E | Y | H | SEQ ID NO: 96 |
| V | D | A | P | L | K | S | P | L | T | A | A | SEQ ID NO: 12 |
| V | M | R | T | D | N | Y | A | P | N | T | L | SEQ ID NO: 97 |

Production of Fusion Protein and Peptide-Displaying Phage Reagents to Validate in vivo Targeting of ADT-Damaged Prostate Microvasculature. The format in which the peptide is displayed, as a free peptide chain anchored at the 3'-terminus on the amino-terminus of the pIII protein on the M13 phage coat, suggests that peptides identified in this protocol are immediately applicable to targeting imaging/therapeutic agents to ADT-damaged prostate microvasculature after covalent attachment to platelets, or more importantly, conjugation to gold-nanoparticles that have been chemically derivatized to provide receptor sites to maximize covalent binding of targeting moieties. Table 5 summarizes t production of stocks of M13 phage displaying the individual peptides, and the production and isolation of stocks of fusion protein (peptide fused to maltose binding protein). All of the peptides have been cloned into a shuttle vector, and subsequently recloned into the expression vector with the maltose binding fusion protein (pMAL-PIII) and into the phage genome (M13KE). The success of cloning into both vectors was verified by DNA sequencing. Some of the phage stocks expressing individual peptides have been expanded, clones picked and sequence verified, and the clonal phage population expanded to a sufficient level that phage were frozen. Eight of the expression constructs for the fusion protein have been expanded in bacterial cultures and the fusion protein isolated using the specific affinity column (yields listed in table). The protein yields are greater than expected. Several of the remaining expression vectors have been propagated large scale cultures and can be readily produced.

TABLE 5

PEPTIDES SPECIFIC FOR IN VIVO TARGETS DURING THE "THERAPEUTIC WINDOW"

| | Duplex Formed | Duplex Digested | Sequence Verified in pMAL Vector | Sequence Verified in M13KE Vector | Phage Amplification (ready for staining) | Protein Expressed |
|---|---|---|---|---|---|---|
| AELLKLFSKSHT (SEQ ID NO: 11) | X | X | X | X | X | 3 mg |
| AGNGTATATERT (SEQ ID NO: 13) | X | X | X | X | X | 5.0 MG |
| APGTLPWASSNR (SEQ ID NO: 2) | X | X | X | X | X | 8.5 mg |
| DAQSIYHFALAP (SEQ ID NO: 3) | X | X | X | X | X | 6.9 mg |
| DPKFPQNSHLIT (SEQ ID NO: 4) | X | X | X | X | X | 3.7 MG |
| GAMHLPWHMGTL (SEQ ID NO: 5) | X | X | x | X | X | 6.7 MG |
| HGLPVTTRGAFG (SEQ ID NO: 14) | X | X | x | x | X | 3.9 MG |

TABLE 5 -continued

PEPTIDES SPECIFIC FOR IN VIVO TARGETS DURING THE "THERAPEUTIC WINDOW"

| | Duplex Formed | Duplex Digested | Sequence Verified in pMAL Vector | Sequence Verified in M13KE Vector | Phage Amplification (ready for staining) | Protein Expressed |
|---|---|---|---|---|---|---|
| KPPQNTSAPYLP (SEQ ID NO: 6) | X | X | X | X | XX | 3.6 mg |
| RLVNSSYLQLAS (SEQ ID NO: 15) | X | X | X | X | X | 2.6 mg |
| SFRTLTDWNVTL (SEQ ID NO: 16) | X | X | X | X | X | 4.1 MG |
| SHAHNSTTFLLA (SEQ ID NO: 7) | X | X | X | X | X | 6.2 MG |
| SPHWQPNAIFVN (SEQ ID NO: 8) | X | X | X | X | X | 5.8 MG |
| SPPPSHPSSGYL (SEQ ID NO: 17) | X | X | X | X | X | 11.7 mg |
| THHHVTYWRSEA (SEQ ID NO: 18) | X | X | X | X | X | 3.1 MG |
| TLQRTHFPPAFS (SEQ ID NO: 9) | X | X | X | X | X | 10.5 mg |
| TMGFTAPRFPHY (SEQ ID NO: 10) | X | X | X | X | X | 6.4 MG |
| VDAPLKSPLTAA (SEQ ID NO: 12) | X | X | X | X | X | 7 MG |

X-Finished

Those skilled in the art will recognize from the foregoing that the present disclosure includes a variety of peptides which will have specific utility for targeting specific binding partners that are present during the transient therapeutic window following androgen deprivation. It will also be recognized that the foregoing description of specific embodiments is for the purpose of illustration and is not to be construed as restrictive. From the teachings of the present invention, those skilled in the art will recognize that various modifications and changes may be made without departing from the spirit of the invention.

We claim:

1. A method of forming a complex comprising a peptide, wherein the amino acid sequence of the peptide consists of TLQRTHFPPAFS (SEQ ID NO:9), the method comprising contacting a human endothelial cell or vascular basement membrane in human prostate tissue with the peptide such that a complex comprising the human endothelial cell or vascular basement membrane and the peptide is formed.

2. The method of claim 1, wherein the peptide comprises a detectable label.

3. The method of claim 2, wherein the detectable label is a radiolabel.

4. The method of claim 1, wherein the peptide is conjugated to a chemotherapeutic agent.

5. The method of claim 1, wherein the peptide is conjugated to a gold nanoparticle.

* * * * *

```
                        SEQUENCE LISTING

<160> NUMBER OF SEQ ID NOS: 101

<210> SEQ ID NO 1
<211> LENGTH: 12
<212> TYPE: PRT
<213> ORGANISM: artificial sequence
<220> FEATURE:
<223> OTHER INFORMATION: Peptide

<400> SEQUENCE: 1

Ala Glu Thr Val Glu Ser Cys Leu Ala Lys Ser His
1               5                   10

<210> SEQ ID NO 2
<211> LENGTH: 12
<212> TYPE: PRT
<213> ORGANISM: artificial sequence
<220> FEATURE:
<223> OTHER INFORMATION: Peptide

<400> SEQUENCE: 2

Ala Pro Gly Thr Leu Pro Trp Ala Ser Ser Asn Arg
```

```
1               5                   10

<210> SEQ ID NO 3
<211> LENGTH: 12
<212> TYPE: PRT
<213> ORGANISM: artificial sequence
<220> FEATURE:
<223> OTHER INFORMATION: Peptide

<400> SEQUENCE: 3

Asp Ala Gln Ser Ile Tyr His Phe Ala Leu Ala Pro
1               5                   10

<210> SEQ ID NO 4
<211> LENGTH: 12
<212> TYPE: PRT
<213> ORGANISM: artificial sequence
<220> FEATURE:
<223> OTHER INFORMATION: Peptide

<400> SEQUENCE: 4

Asp Pro Lys Phe Pro Gln Asn Ser His Leu Ile Thr
1               5                   10

<210> SEQ ID NO 5
<211> LENGTH: 12
<212> TYPE: PRT
<213> ORGANISM: artificial sequence
<220> FEATURE:
<223> OTHER INFORMATION: Peptide

<400> SEQUENCE: 5

Gly Ala Met His Leu Pro Trp His Met Gly Thr Leu
1               5                   10

<210> SEQ ID NO 6
<211> LENGTH: 12
<212> TYPE: PRT
<213> ORGANISM: artificial sequence
<220> FEATURE:
<223> OTHER INFORMATION: Peptide

<400> SEQUENCE: 6

Lys Pro Pro Gln Asn Thr Ser Ala Pro Tyr Leu Pro
1               5                   10

<210> SEQ ID NO 7
<211> LENGTH: 12
<212> TYPE: PRT
<213> ORGANISM: artificial sequence
<220> FEATURE:
<223> OTHER INFORMATION: Peptide

<400> SEQUENCE: 7

Ser His Ala His Asn Ser Thr Thr Phe Leu Leu Ala
1               5                   10

<210> SEQ ID NO 8
<211> LENGTH: 12
<212> TYPE: PRT
<213> ORGANISM: artificial sequence
<220> FEATURE:
<223> OTHER INFORMATION: Peptide

<400> SEQUENCE: 8

Ser Pro His Trp Gln Pro Asn Ala Ile Phe Val Asn
1               5                   10
```

```
<210> SEQ ID NO 9
<211> LENGTH: 12
<212> TYPE: PRT
<213> ORGANISM: artificial sequence
<220> FEATURE:
<223> OTHER INFORMATION: Peptide

<400> SEQUENCE: 9

Thr Leu Gln Arg Thr His Phe Pro Pro Ala Phe Ser
1               5                   10

<210> SEQ ID NO 10
<211> LENGTH: 12
<212> TYPE: PRT
<213> ORGANISM: artificial sequence
<220> FEATURE:
<223> OTHER INFORMATION: Peptide

<400> SEQUENCE: 10

Thr Met Gly Phe Thr Ala Pro Arg Phe Pro His Tyr
1               5                   10

<210> SEQ ID NO 11
<211> LENGTH: 12
<212> TYPE: PRT
<213> ORGANISM: artificial sequence
<220> FEATURE:
<223> OTHER INFORMATION: Peptide

<400> SEQUENCE: 11

Ala Glu Leu Leu Lys Leu Phe Ser Lys Ser His Thr
1               5                   10

<210> SEQ ID NO 12
<211> LENGTH: 12
<212> TYPE: PRT
<213> ORGANISM: artificial sequence
<220> FEATURE:
<223> OTHER INFORMATION: Peptide

<400> SEQUENCE: 12

Val Asp Ala Pro Leu Lys Ser Pro Leu Thr Ala Ala
1               5                   10

<210> SEQ ID NO 13
<211> LENGTH: 12
<212> TYPE: PRT
<213> ORGANISM: artificial sequence
<220> FEATURE:
<223> OTHER INFORMATION: Peptide

<400> SEQUENCE: 13

Ala Gly Asn Gly Thr Ala Thr Ala Thr Glu Arg Thr
1               5                   10

<210> SEQ ID NO 14
<211> LENGTH: 12
<212> TYPE: PRT
<213> ORGANISM: artificial sequence
<220> FEATURE:
<223> OTHER INFORMATION: Peptide

<400> SEQUENCE: 14

His Gly Leu Pro Val Thr Thr Arg Gly Ala Phe Gly
1               5                   10
```

<210> SEQ ID NO 15
<211> LENGTH: 12
<212> TYPE: PRT
<213> ORGANISM: artificial sequence
<220> FEATURE:
<223> OTHER INFORMATION: Peptide

<400> SEQUENCE: 15

Arg Leu Val Asn Ser Ser Tyr Leu Gln Leu Ala Ser
1               5                   10

<210> SEQ ID NO 16
<211> LENGTH: 12
<212> TYPE: PRT
<213> ORGANISM: artificial sequence
<220> FEATURE:
<223> OTHER INFORMATION: Peptide

<400> SEQUENCE: 16

Ser Phe Arg Thr Leu Thr Asp Trp Asn Val Thr Leu
1               5                   10

<210> SEQ ID NO 17
<211> LENGTH: 12
<212> TYPE: PRT
<213> ORGANISM: artificial sequence
<220> FEATURE:
<223> OTHER INFORMATION: Peptide

<400> SEQUENCE: 17

Ser Pro Pro Pro Ser His Pro Ser Ser Gly Tyr Leu
1               5                   10

<210> SEQ ID NO 18
<211> LENGTH: 12
<212> TYPE: PRT
<213> ORGANISM: artificial sequence
<220> FEATURE:
<223> OTHER INFORMATION: Peptide

<400> SEQUENCE: 18

Thr His His His Val Thr Tyr Trp Arg Ser Glu Ala
1               5                   10

<210> SEQ ID NO 19
<211> LENGTH: 9
<212> TYPE: PRT
<213> ORGANISM: artificial sequence
<220> FEATURE:
<223> OTHER INFORMATION: Peptide

<400> SEQUENCE: 19

Ser Pro His Trp Gln Pro Asn Ala Ile
1               5

<210> SEQ ID NO 20
<211> LENGTH: 13
<212> TYPE: PRT
<213> ORGANISM: artificial sequence
<220> FEATURE:
<223> OTHER INFORMATION: Peptide

<400> SEQUENCE: 20

Lys Pro Pro Gln Thr Asn Thr Ser Ala Pro Tyr Leu Pro
1               5                   10

```
<210> SEQ ID NO 21
<211> LENGTH: 11
<212> TYPE: PRT
<213> ORGANISM: artificial sequence
<220> FEATURE:
<223> OTHER INFORMATION: Peptide

<400> SEQUENCE: 21

Asp Gln His Gly Phe Met His Ile Phe Asp Leu
1               5                   10

<210> SEQ ID NO 22
<211> LENGTH: 12
<212> TYPE: PRT
<213> ORGANISM: artificial sequence
<220> FEATURE:
<223> OTHER INFORMATION: Peptide

<400> SEQUENCE: 22

His Ser Ala Gln Pro Val Lys Ser Lys Ala Trp Leu
1               5                   10

<210> SEQ ID NO 23
<211> LENGTH: 11
<212> TYPE: PRT
<213> ORGANISM: artificial sequence
<220> FEATURE:
<223> OTHER INFORMATION: Peptide

<400> SEQUENCE: 23

Leu Leu Ala Asp Thr Thr His His Arg Trp Thr
1               5                   10

<210> SEQ ID NO 24
<211> LENGTH: 12
<212> TYPE: PRT
<213> ORGANISM: artificial sequence
<220> FEATURE:
<223> OTHER INFORMATION: Peptide

<400> SEQUENCE: 24

Thr Leu Gln Arg Thr His Phe Pro Pro Ala Phe Arg
1               5                   10

<210> SEQ ID NO 25
<211> LENGTH: 12
<212> TYPE: PRT
<213> ORGANISM: artificial sequence
<220> FEATURE:
<223> OTHER INFORMATION: Peptide

<400> SEQUENCE: 25

Thr Leu Gln Arg Thr His Phe Ser Ala Gly Val Phe
1               5                   10

<210> SEQ ID NO 26
<211> LENGTH: 12
<212> TYPE: PRT
<213> ORGANISM: artificial sequence
<220> FEATURE:
<223> OTHER INFORMATION: Peptide

<400> SEQUENCE: 26

Thr Leu Gln Arg Thr His Phe Arg Arg Arg Phe Gly
1               5                   10

<210> SEQ ID NO 27
```

```
<211> LENGTH: 10
<212> TYPE: PRT
<213> ORGANISM: artificial sequence
<220> FEATURE:
<223> OTHER INFORMATION: Peptide

<400> SEQUENCE: 27

Thr Leu Gln Arg Thr His Phe Pro Ser Gly
1               5                   10

<210> SEQ ID NO 28
<211> LENGTH: 12
<212> TYPE: PRT
<213> ORGANISM: artificial sequence
<220> FEATURE:
<223> OTHER INFORMATION: Peptide

<400> SEQUENCE: 28

Thr Leu Gln Arg Thr His Phe Pro Ser Gly Val Phe
1               5                   10

<210> SEQ ID NO 29
<211> LENGTH: 12
<212> TYPE: PRT
<213> ORGANISM: artificial sequence
<220> FEATURE:
<223> OTHER INFORMATION: Peptide

<400> SEQUENCE: 29

Thr Leu Gln Arg Thr Leu Phe Ser Ala Gly Arg Phe
1               5                   10

<210> SEQ ID NO 30
<211> LENGTH: 10
<212> TYPE: PRT
<213> ORGANISM: artificial sequence
<220> FEATURE:
<223> OTHER INFORMATION: Peptide

<400> SEQUENCE: 30

Thr Leu Gln Arg Thr His Phe Pro Pro Ala
1               5                   10

<210> SEQ ID NO 31
<211> LENGTH: 12
<212> TYPE: PRT
<213> ORGANISM: artificial sequence
<220> FEATURE:
<223> OTHER INFORMATION: Peptide

<400> SEQUENCE: 31

Thr Leu Gln Arg Thr His Phe Pro Pro Ala Phe Phe
1               5                   10

<210> SEQ ID NO 32
<211> LENGTH: 12
<212> TYPE: PRT
<213> ORGANISM: artificial sequence
<220> FEATURE:
<223> OTHER INFORMATION: Peptide

<400> SEQUENCE: 32

Thr Leu Gln Arg Thr His Phe Arg Pro Ala Phe Arg
1               5                   10

<210> SEQ ID NO 33
<211> LENGTH: 12
```

```
<212> TYPE: PRT
<213> ORGANISM: artificial sequence
<220> FEATURE:
<223> OTHER INFORMATION: Peptide

<400> SEQUENCE: 33

Thr Leu Gln Arg Thr His Phe Pro Pro Val Val Phe
1               5                   10

<210> SEQ ID NO 34
<211> LENGTH: 11
<212> TYPE: PRT
<213> ORGANISM: artificial sequence
<220> FEATURE:
<223> OTHER INFORMATION: Peptide

<400> SEQUENCE: 34

Thr Leu Gln Arg Thr His Phe Pro Ser Gly Val
1               5                   10

<210> SEQ ID NO 35
<211> LENGTH: 12
<212> TYPE: PRT
<213> ORGANISM: artificial sequence
<220> FEATURE:
<223> OTHER INFORMATION: Peptide

<400> SEQUENCE: 35

Thr Leu Gln Arg Thr His Phe Pro Ser Gly Val Ser
1               5                   10

<210> SEQ ID NO 36
<211> LENGTH: 12
<212> TYPE: PRT
<213> ORGANISM: artificial sequence
<220> FEATURE:
<223> OTHER INFORMATION: Peptide

<400> SEQUENCE: 36

Thr Leu Gln Arg Thr Leu Phe Pro Pro Val Val Ser
1               5                   10

<210> SEQ ID NO 37
<211> LENGTH: 12
<212> TYPE: PRT
<213> ORGANISM: artificial sequence
<220> FEATURE:
<223> OTHER INFORMATION: Peptide

<400> SEQUENCE: 37

Thr Leu Gln Arg Thr Leu Phe Ser Ala Gly Val Phe
1               5                   10

<210> SEQ ID NO 38
<211> LENGTH: 12
<212> TYPE: PRT
<213> ORGANISM: artificial sequence
<220> FEATURE:
<223> OTHER INFORMATION: Peptide

<400> SEQUENCE: 38

Thr Leu Gln Arg Thr His Phe Pro Pro Val Val Ser
1               5                   10

<210> SEQ ID NO 39
<211> LENGTH: 12
<212> TYPE: PRT
```

```
<213> ORGANISM: artificial sequence
<220> FEATURE:
<223> OTHER INFORMATION: Peptide

<400> SEQUENCE: 39

Thr Leu Gln Arg Thr His Phe Pro Arg Phe Arg
1               5                   10

<210> SEQ ID NO 40
<211> LENGTH: 10
<212> TYPE: PRT
<213> ORGANISM: artificial sequence
<220> FEATURE:
<223> OTHER INFORMATION: Peptide

<400> SEQUENCE: 40

Thr Leu Gln Arg Thr His Phe Pro Ser Ala
1               5                   10

<210> SEQ ID NO 41
<211> LENGTH: 11
<212> TYPE: PRT
<213> ORGANISM: artificial sequence
<220> FEATURE:
<223> OTHER INFORMATION: Peptide

<400> SEQUENCE: 41

Thr Leu Gln Arg Thr His Phe Arg Pro Ala Phe
1               5                   10

<210> SEQ ID NO 42
<211> LENGTH: 12
<212> TYPE: PRT
<213> ORGANISM: artificial sequence
<220> FEATURE:
<223> OTHER INFORMATION: Peptide

<400> SEQUENCE: 42

Thr Leu Gln Arg Thr His Phe Pro Pro Gly Val Phe
1               5                   10

<210> SEQ ID NO 43
<211> LENGTH: 11
<212> TYPE: PRT
<213> ORGANISM: artificial sequence
<220> FEATURE:
<223> OTHER INFORMATION: Peptide

<400> SEQUENCE: 43

Thr Leu Gln Arg Thr His Phe Arg Arg Arg Phe
1               5                   10

<210> SEQ ID NO 44
<211> LENGTH: 12
<212> TYPE: PRT
<213> ORGANISM: artificial sequence
<220> FEATURE:
<223> OTHER INFORMATION: Peptide

<400> SEQUENCE: 44

Thr Leu Gln Arg Ile His Phe Pro Pro Ala Phe Ser
1               5                   10

<210> SEQ ID NO 45
<211> LENGTH: 12
<212> TYPE: PRT
<213> ORGANISM: artificial sequence
```

<220> FEATURE:
<223> OTHER INFORMATION: Peptide

<400> SEQUENCE: 45

Thr Leu Gln Arg Thr His Phe Ser Pro Ala Phe Ser
1               5                   10

<210> SEQ ID NO 46
<211> LENGTH: 10
<212> TYPE: PRT
<213> ORGANISM: artificial sequence
<220> FEATURE:
<223> OTHER INFORMATION: Peptide

<400> SEQUENCE: 46

Thr Leu Gln Arg Thr His Phe Ser Val Arg
1               5                   10

<210> SEQ ID NO 47
<211> LENGTH: 12
<212> TYPE: PRT
<213> ORGANISM: artificial sequence
<220> FEATURE:
<223> OTHER INFORMATION: Peptide

<400> SEQUENCE: 47

Thr Leu Gln Arg Thr His Phe Pro Pro Ala Phe Trp
1               5                   10

<210> SEQ ID NO 48
<211> LENGTH: 12
<212> TYPE: PRT
<213> ORGANISM: artificial sequence
<220> FEATURE:
<223> OTHER INFORMATION: Peptide

<400> SEQUENCE: 48

Thr Leu Gln Arg Thr His Phe Pro Pro Ala Phe Pro
1               5                   10

<210> SEQ ID NO 49
<211> LENGTH: 12
<212> TYPE: PRT
<213> ORGANISM: artificial sequence
<220> FEATURE:
<223> OTHER INFORMATION: Peptide

<400> SEQUENCE: 49

Thr Leu Gln Arg Thr His Phe Pro Pro Ala Ala Gly
1               5                   10

<210> SEQ ID NO 50
<211> LENGTH: 12
<212> TYPE: PRT
<213> ORGANISM: artificial sequence
<220> FEATURE:
<223> OTHER INFORMATION: Peptide

<400> SEQUENCE: 50

Thr Leu Gln Arg Thr His Phe Pro Pro Ala Arg Arg
1               5                   10

<210> SEQ ID NO 51
<211> LENGTH: 12
<212> TYPE: PRT
<213> ORGANISM: artificial sequence
<220> FEATURE:

<223> OTHER INFORMATION: Peptide

<400> SEQUENCE: 51

Thr Leu Gln Arg Thr His Phe Pro Leu Ala Phe Ser
1               5                   10

<210> SEQ ID NO 52
<211> LENGTH: 12
<212> TYPE: PRT
<213> ORGANISM: artificial sequence
<220> FEATURE:
<223> OTHER INFORMATION: Peptide

<400> SEQUENCE: 52

Thr Leu Gln Arg Thr His Phe Pro Arg Leu Phe Gly
1               5                   10

<210> SEQ ID NO 53
<211> LENGTH: 12
<212> TYPE: PRT
<213> ORGANISM: artificial sequence
<220> FEATURE:
<223> OTHER INFORMATION: Peptide

<400> SEQUENCE: 53

Thr Leu Gln Arg Thr His Phe Pro Arg Arg Phe Gly
1               5                   10

<210> SEQ ID NO 54
<211> LENGTH: 12
<212> TYPE: PRT
<213> ORGANISM: artificial sequence
<220> FEATURE:
<223> OTHER INFORMATION: Peptide

<400> SEQUENCE: 54

Ser Pro His Trp Gln Pro Asn Ala Ile Leu Leu Met
1               5                   10

<210> SEQ ID NO 55
<211> LENGTH: 11
<212> TYPE: PRT
<213> ORGANISM: artificial sequence
<220> FEATURE:
<223> OTHER INFORMATION: Peptide

<400> SEQUENCE: 55

Ser Pro His Trp Gln Pro Asn Ala Ile Leu Leu
1               5                   10

<210> SEQ ID NO 56
<211> LENGTH: 10
<212> TYPE: PRT
<213> ORGANISM: artificial sequence
<220> FEATURE:
<223> OTHER INFORMATION: Peptide

<400> SEQUENCE: 56

Ser Pro His Trp Gln Pro Asn Ala Ile Leu
1               5                   10

<210> SEQ ID NO 57
<211> LENGTH: 12
<212> TYPE: PRT
<213> ORGANISM: artificial sequence
<220> FEATURE:
<223> OTHER INFORMATION: Peptide

<400> SEQUENCE: 57

Lys Pro Pro Gln Asn Thr Ser Ala Pro Leu Ser Ser
1               5                   10

<210> SEQ ID NO 58
<211> LENGTH: 12
<212> TYPE: PRT
<213> ORGANISM: artificial sequence
<220> FEATURE:
<223> OTHER INFORMATION: Peptide

<400> SEQUENCE: 58

Lys Pro Pro Gln Asn Thr Ser Ala Pro Tyr Leu Arg
1               5                   10

<210> SEQ ID NO 59
<211> LENGTH: 10
<212> TYPE: PRT
<213> ORGANISM: artificial sequence
<220> FEATURE:
<223> OTHER INFORMATION: Peptide

<400> SEQUENCE: 59

Lys Pro Pro Gln Asn Thr Ser Ala Pro Tyr
1               5                   10

<210> SEQ ID NO 60
<211> LENGTH: 12
<212> TYPE: PRT
<213> ORGANISM: artificial sequence
<220> FEATURE:
<223> OTHER INFORMATION: Peptide

<400> SEQUENCE: 60

Lys Pro Pro Gln Asn Thr Ser Cys Ala Phe Ile Phe
1               5                   10

<210> SEQ ID NO 61
<211> LENGTH: 12
<212> TYPE: PRT
<213> ORGANISM: artificial sequence
<220> FEATURE:
<223> OTHER INFORMATION: Peptide

<400> SEQUENCE: 61

Thr Met Gly Phe Thr Ala Pro Arg Phe Pro Ser Leu
1               5                   10

<210> SEQ ID NO 62
<211> LENGTH: 12
<212> TYPE: PRT
<213> ORGANISM: artificial sequence
<220> FEATURE:
<223> OTHER INFORMATION: Peptide

<400> SEQUENCE: 62

Thr Met Gly Phe Thr Ala Pro Arg Phe Ser Ala Leu
1               5                   10

<210> SEQ ID NO 63
<211> LENGTH: 12
<212> TYPE: PRT
<213> ORGANISM: artificial sequence
<220> FEATURE:
<223> OTHER INFORMATION: Peptide

<400> SEQUENCE: 63

Thr Met Gly Leu Thr His Ser Arg Val Arg Ile Glu
1               5                   10

<210> SEQ ID NO 64
<211> LENGTH: 12
<212> TYPE: PRT
<213> ORGANISM: artificial sequence
<220> FEATURE:
<223> OTHER INFORMATION: Peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 64

Thr Xaa Gly Phe Thr Ala Pro Arg Phe Pro His Tyr
1               5                   10

<210> SEQ ID NO 65
<211> LENGTH: 12
<212> TYPE: PRT
<213> ORGANISM: artificial sequence
<220> FEATURE:
<223> OTHER INFORMATION: Peptide

<400> SEQUENCE: 65

Thr Met Gly Phe Thr Ala Pro Arg Phe Pro Ser Leu
1               5                   10

<210> SEQ ID NO 66
<211> LENGTH: 12
<212> TYPE: PRT
<213> ORGANISM: artificial sequence
<220> FEATURE:
<223> OTHER INFORMATION: Peptide

<400> SEQUENCE: 66

Thr Met Gly Phe Thr Ala Pro Arg Phe Ser Ala Leu
1               5                   10

<210> SEQ ID NO 67
<211> LENGTH: 10
<212> TYPE: PRT
<213> ORGANISM: artificial sequence
<220> FEATURE:
<223> OTHER INFORMATION: Peptide

<400> SEQUENCE: 67

Thr Met Gly Phe Thr Ala Pro Arg Phe Pro
1               5                   10

<210> SEQ ID NO 68
<211> LENGTH: 12
<212> TYPE: PRT
<213> ORGANISM: artificial sequence
<220> FEATURE:
<223> OTHER INFORMATION: Peptide

<400> SEQUENCE: 68

Thr Met Gly Phe Thr Ala Pro Arg Phe Pro His Gln
1               5                   10

<210> SEQ ID NO 69
<211> LENGTH: 12
<212> TYPE: PRT
<213> ORGANISM: artificial sequence
<220> FEATURE:
<223> OTHER INFORMATION: Peptide

<400> SEQUENCE: 69

Thr Met Gly Phe Thr Ala Pro Arg Phe Pro Leu Leu
1               5                   10

<210> SEQ ID NO 70
<211> LENGTH: 12
<212> TYPE: PRT
<213> ORGANISM: artificial sequence
<220> FEATURE:
<223> OTHER INFORMATION: Peptide

<400> SEQUENCE: 70

Thr Met Gly Phe Thr Ala Pro Arg Phe Arg Ile Met
1               5                   10

<210> SEQ ID NO 71
<211> LENGTH: 12
<212> TYPE: PRT
<213> ORGANISM: artificial sequence
<220> FEATURE:
<223> OTHER INFORMATION: Peptide

<400> SEQUENCE: 71

Thr Met Gly Phe Thr Ala Pro Arg Phe Pro His Leu
1               5                   10

<210> SEQ ID NO 72
<211> LENGTH: 12
<212> TYPE: PRT
<213> ORGANISM: artificial sequence
<220> FEATURE:
<223> OTHER INFORMATION: Peptide

<400> SEQUENCE: 72

Thr Met Gly Phe Thr Ala Pro Arg Phe Pro His Arg
1               5                   10

<210> SEQ ID NO 73
<211> LENGTH: 12
<212> TYPE: PRT
<213> ORGANISM: artificial sequence
<220> FEATURE:
<223> OTHER INFORMATION: Peptide

<400> SEQUENCE: 73

Thr Met Gly Phe Thr Ala Pro Arg Phe Pro His His
1               5                   10

<210> SEQ ID NO 74
<211> LENGTH: 12
<212> TYPE: PRT
<213> ORGANISM: artificial sequence
<220> FEATURE:
<223> OTHER INFORMATION: Peptide

<400> SEQUENCE: 74

Thr Met Gly Phe Thr Ala Pro Arg Phe Pro Ser Val
1               5                   10

<210> SEQ ID NO 75
<211> LENGTH: 12
<212> TYPE: PRT
<213> ORGANISM: artificial sequence
<220> FEATURE:

<223> OTHER INFORMATION: Peptide

<400> SEQUENCE: 75

Thr Met Gly Phe Thr Ala Pro Arg Phe Pro Ala Leu
1               5                   10

<210> SEQ ID NO 76
<211> LENGTH: 12
<212> TYPE: PRT
<213> ORGANISM: artificial sequence
<220> FEATURE:
<223> OTHER INFORMATION: Peptide

<400> SEQUENCE: 76

Thr Met Gly Phe Thr Ala Pro Arg Phe Pro His Cys
1               5                   10

<210> SEQ ID NO 77
<211> LENGTH: 12
<212> TYPE: PRT
<213> ORGANISM: artificial sequence
<220> FEATURE:
<223> OTHER INFORMATION: Peptide

<400> SEQUENCE: 77

Thr Met Gly Phe Thr Ala Pro Arg Phe Pro His Met
1               5                   10

<210> SEQ ID NO 78
<211> LENGTH: 12
<212> TYPE: PRT
<213> ORGANISM: artificial sequence
<220> FEATURE:
<223> OTHER INFORMATION: Peptide

<400> SEQUENCE: 78

Thr Met Gly Phe Thr Ala Pro Arg Phe Gln His Tyr
1               5                   10

<210> SEQ ID NO 79
<211> LENGTH: 12
<212> TYPE: PRT
<213> ORGANISM: artificial sequence
<220> FEATURE:
<223> OTHER INFORMATION: Peptide

<400> SEQUENCE: 79

Thr Met Gly Phe Thr Ala Pro Arg Arg Gly Ala Val
1               5                   10

<210> SEQ ID NO 80
<211> LENGTH: 12
<212> TYPE: PRT
<213> ORGANISM: artificial sequence
<220> FEATURE:
<223> OTHER INFORMATION: Peptide

<400> SEQUENCE: 80

Thr Met Gly Phe Thr Ala Pro Trp Phe Pro His Tyr
1               5                   10

<210> SEQ ID NO 81
<211> LENGTH: 12
<212> TYPE: PRT
<213> ORGANISM: artificial sequence
<220> FEATURE:
<223> OTHER INFORMATION: Peptide

<400> SEQUENCE: 81

Ala His Thr Thr Asn Ser Ser Asn Tyr Arg Phe Thr
1               5                   10

<210> SEQ ID NO 82
<211> LENGTH: 12
<212> TYPE: PRT
<213> ORGANISM: artificial sequence
<220> FEATURE:
<223> OTHER INFORMATION: Peptide

<400> SEQUENCE: 82

Asp Pro Ser Leu Asp Asn His Ser Gly Pro Ile Lys
1               5                   10

<210> SEQ ID NO 83
<211> LENGTH: 12
<212> TYPE: PRT
<213> ORGANISM: artificial sequence
<220> FEATURE:
<223> OTHER INFORMATION: Peptide

<400> SEQUENCE: 83

Glu Ala Ala Ile Thr Leu Pro Met Thr Ser Trp Thr
1               5                   10

<210> SEQ ID NO 84
<211> LENGTH: 12
<212> TYPE: PRT
<213> ORGANISM: artificial sequence
<220> FEATURE:
<223> OTHER INFORMATION: Peptide

<400> SEQUENCE: 84

Glu Leu Ser Thr Lys Pro Lys Ala Val Val Pro Tyr
1               5                   10

<210> SEQ ID NO 85
<211> LENGTH: 12
<212> TYPE: PRT
<213> ORGANISM: artificial sequence
<220> FEATURE:
<223> OTHER INFORMATION: Peptide

<400> SEQUENCE: 85

Gly Ser Glu Ser Ser His Leu Tyr Glu Lys Pro Lys
1               5                   10

<210> SEQ ID NO 86
<211> LENGTH: 12
<212> TYPE: PRT
<213> ORGANISM: artificial sequence
<220> FEATURE:
<223> OTHER INFORMATION: Peptide

<400> SEQUENCE: 86

Ile Pro Ala Pro Ala Ser Met Leu Lys Pro Pro Arg
1               5                   10

<210> SEQ ID NO 87
<211> LENGTH: 12
<212> TYPE: PRT
<213> ORGANISM: artificial sequence
<220> FEATURE:
<223> OTHER INFORMATION: Peptide

```
<400> SEQUENCE: 87

Lys Pro His Phe Leu Asn Gln Ser Gly Ser Tyr Ile
1               5                   10

<210> SEQ ID NO 88
<211> LENGTH: 12
<212> TYPE: PRT
<213> ORGANISM: artificial sequence
<220> FEATURE:
<223> OTHER INFORMATION: Peptide

<400> SEQUENCE: 88

Leu Pro Tyr Arg Thr Thr His Ile Gly Pro Leu Pro
1               5                   10

<210> SEQ ID NO 89
<211> LENGTH: 12
<212> TYPE: PRT
<213> ORGANISM: artificial sequence
<220> FEATURE:
<223> OTHER INFORMATION: Peptide

<400> SEQUENCE: 89

Leu Gln Ser Thr Ser Pro Ala Tyr Thr His Arg Met
1               5                   10

<210> SEQ ID NO 90
<211> LENGTH: 12
<212> TYPE: PRT
<213> ORGANISM: artificial sequence
<220> FEATURE:
<223> OTHER INFORMATION: Peptide

<400> SEQUENCE: 90

Asn His Ala Val Asn Lys Trp Thr Leu Ser His Ala
1               5                   10

<210> SEQ ID NO 91
<211> LENGTH: 12
<212> TYPE: PRT
<213> ORGANISM: artificial sequence
<220> FEATURE:
<223> OTHER INFORMATION: Peptide

<400> SEQUENCE: 91

Gln Pro Arg Pro Thr Gln Tyr Gln Glu His Ser Ala
1               5                   10

<210> SEQ ID NO 92
<211> LENGTH: 12
<212> TYPE: PRT
<213> ORGANISM: artificial sequence
<220> FEATURE:
<223> OTHER INFORMATION: Peptide

<400> SEQUENCE: 92

Gln Leu Thr Gly Pro Thr Gly Met Lys Thr Pro Leu
1               5                   10

<210> SEQ ID NO 93
<211> LENGTH: 12
<212> TYPE: PRT
<213> ORGANISM: artificial sequence
<220> FEATURE:
<223> OTHER INFORMATION: Peptide
<220> FEATURE:
<221> NAME/KEY: misc_feature
```

```
<222> LOCATION: (10)..(12)
<223> OTHER INFORMATION: Xaa can be any naturally occurring amino acid

<400> SEQUENCE: 93

Ser His Ala His Asn Ser Thr Thr Phe Xaa Xaa Xaa
1               5                   10

<210> SEQ ID NO 94
<211> LENGTH: 12
<212> TYPE: PRT
<213> ORGANISM: artificial sequence
<220> FEATURE:
<223> OTHER INFORMATION: Peptide

<400> SEQUENCE: 94

Ser Thr Ala Gly Pro Met Phe Pro Gln Gln Ser Arg
1               5                   10

<210> SEQ ID NO 95
<211> LENGTH: 12
<212> TYPE: PRT
<213> ORGANISM: artificial sequence
<220> FEATURE:
<223> OTHER INFORMATION: Peptide

<400> SEQUENCE: 95

Thr His Pro Gly Ser Ser Met Arg His Thr His His
1               5                   10

<210> SEQ ID NO 96
<211> LENGTH: 12
<212> TYPE: PRT
<213> ORGANISM: artificial sequence
<220> FEATURE:
<223> OTHER INFORMATION: Peptide

<400> SEQUENCE: 96

Thr His Ser His Gly Leu Lys Pro Ser Glu Tyr His
1               5                   10

<210> SEQ ID NO 97
<211> LENGTH: 12
<212> TYPE: PRT
<213> ORGANISM: artificial sequence
<220> FEATURE:
<223> OTHER INFORMATION: Peptide

<400> SEQUENCE: 97

Val Met Arg Thr Asp Asn Tyr Ala Pro Asn Thr Leu
1               5                   10

<210> SEQ ID NO 98
<211> LENGTH: 21
<212> TYPE: DNA
<213> ORGANISM: artificial sequence
<220> FEATURE:
<223> OTHER INFORMATION: Primer

<400> SEQUENCE: 98
cctttctatt ctcactctgc t                                              21

<210> SEQ ID NO 99
<211> LENGTH: 21
<212> TYPE: DNA
<213> ORGANISM: artificial sequence
<220> FEATURE:
<223> OTHER INFORMATION: Primer
```

```
<400> SEQUENCE: 99
ccgtaacact gagtttcgtc a                                      21

<210> SEQ ID NO 100
<211> LENGTH: 11
<212> TYPE: PRT
<213> ORGANISM: artificial sequence
<220> FEATURE:
<223> OTHER INFORMATION: Peptide

<400> SEQUENCE: 100

Gly Ala Met His Leu Pro Trp His Met Gly Thr
1               5                   10

<210> SEQ ID NO 101
<211> LENGTH: 12
<212> TYPE: PRT
<213> ORGANISM: artificial sequence
<220> FEATURE:
<223> OTHER INFORMATION: Peptide

<400> SEQUENCE: 101

Gly Ala Met His Leu Pro Trp His Ile Gly Thr Leu
1               5                   10
```